United States Patent
Al-Ali et al.

(10) Patent No.: US 7,919,713 B2
(45) Date of Patent: Apr. 5, 2011

(54) LOW NOISE OXIMETRY CABLE INCLUDING CONDUCTIVE CORDS

(75) Inventors: Ammar Al-Ali, Tustin, CA (US); John Schmidt, Lake Forest, CA (US); Kevin Forrest, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 272 days.

(21) Appl. No.: 12/104,350

(22) Filed: Apr. 16, 2008

(65) Prior Publication Data

US 2008/0255435 A1  Oct. 16, 2008

Related U.S. Application Data

(60) Provisional application No. 60/912,139, filed on Apr. 16, 2007.

(51) Int. Cl.
*H01B 11/02* (2006.01)
(52) U.S. Cl. .................................................. 174/113 R
(58) Field of Classification Search ............... 174/113 R, 174/47, 105 R
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |

(Continued)

*Primary Examiner* — Chau N Nguyen
(74) *Attorney, Agent, or Firm* — Knobbe Martens, Olson & Bear LLP

(57) ABSTRACT

In an embodiment, one or more conductive cable cords are twisted with the sensitive signal carrying cables. The cords may advantageously comprise dummy wires, or very flexible hollow cables without an inner conductor. As the conductive cords do not carry and inner conductor, the conductive cords are individually flexible and small, resulting in a twisted bundle that more is flexible while potentially having a smaller outer diameter.

11 Claims, 3 Drawing Sheets

U.S. PATENT DOCUMENTS

| | | | |
|---|---|---|---|
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |

| | | |
|---|---|---|
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 2004/0000417 A1* | 1/2004 | Kao .............................. 174/36 |

* cited by examiner

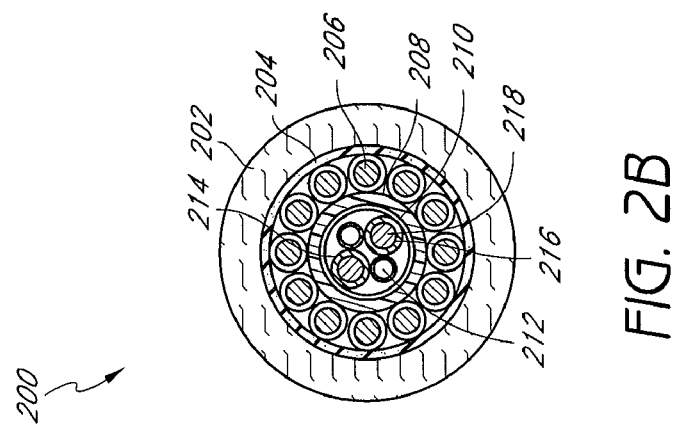
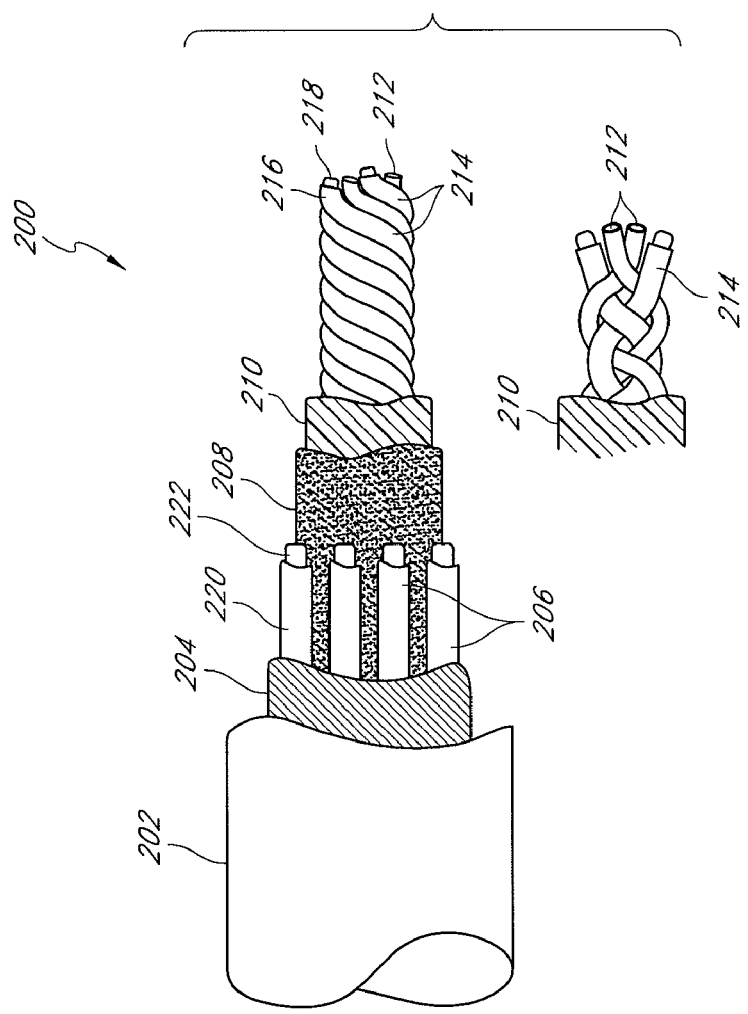
FIG. 2B
FIG. 2A

LOW NOISE OXIMETRY CABLE INCLUDING CONDUCTIVE CORDS

PRIORITY CLAIM

This application claims the benefit of U.S. Provisional Application No. 60/912,139, filed Apr. 16, 2007, entitled "Low Noise Oximetry Cable Including Conductive Cords." The foregoing application is incorporated in its entirety by reference herein.

CROSS-REFERENCE TO RELATED APPLICATIONS

The present application is related to the disclosure of abandoned U.S. patent application Ser. No. 10/325,602, filed on Dec. 19, 2002, titled "Low Noise Patient Cable," which is incorporated herein by reference. Also, pending U.S. patent application Ser. No. 11/367,013, filed Mar. 1, 2006, titled "Multiple Wavelength Sensor Emitters," is incorporated herein by reference.

BACKGROUND OF THE DISCLOSURE

1. Field of the Disclosure

The disclosure relates to improving the performance of patient monitors through low noise cabling.

2. Description of the Related Art

Oximetry utilizes a noninvasive optical sensor to measure physiological parameters of a patient. In general, the sensor has light emitting diodes (LEDs) that transmit optical radiation into a tissue site and a detector that responds to the intensity of the optical radiation after absorption (e.g., by transmission or transreflectance) by, for example, pulsatile arterial blood flowing within the tissue site. Based on this response, a processor determines measurements for oxygen saturation ($SpO_2$), pulse rate, plethysmograph waveforms, perfusion quality index (e.g., an index that quantifies perfusion), assessments of other blood constituents, parameters or analytes, including for example, a percent value for arterial carbon monoxide saturation (HbCO), a percent value for methemoglobin saturation (a brownish-red form of hemoglobin that cannot function as an oxygen carrier) (HbMet), total hemoglobin (HbT), fractional $SpO_2$ ($SpaO_2$) or the like. Additionally, caregivers often desire knowledge of $HbO_2$, Hb, blood glucose (HbGu), water, the presence or absence of therapeutic drugs (aspirin, Dapson, nitrates, or the like) or abusive/recreational drugs (methamphetamine, alcohol, steroids, or the like), concentrations of carbon dioxide ($CO_2$), oxygen ($O_2$), oxygen concentration, pH levels, bilirubin, perfusion quality, albumin, cyanmethemoglobin, and sulfhemoglobin (HbSulf), signal quality or the like. It is noted that "oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood.

Oximeters capable of reading many of the foregoing parameters during motion induced noise are available from Masimo Corporation (Masimo) of Irvine, Calif. Moreover, portable and other oximeters are disclosed in at least U.S. Pat. Nos. 6,770,028, 6,658,276, 6,157,850, 6,002,952, and 5,769,785, incorporated by reference herein, and others patent publications such as those listed at http://www.masimo.com/patents.htm. Such reading through motion oximeters have gained rapid acceptance in a wide variety of medical applications, including surgical wards, intensive care and neonatal units, general wards, home care, physical training, and virtually all types of monitoring scenarios.

The detectors of the noninvasive sensors read by many of the foregoing patient monitors generate one or more low-level signals that are susceptible to corruption from various noise, such as electromagnetic interference (EMI) and internal noise that originate in the sensor, cabling and monitors. One internal noise source is due to a triboelectric effect, which includes static charges that build when two materials rub together. For example, when a cable housing detector wires is flexed, impacted, or the like, the detector wires may rub together and triboelectric noise can be induced in the detector signal. These induced triboelectric noise spikes can be orders of magnitude larger than the desired low level detector signals.

To alleviate the buildup of triboelectric charges, low noise cable manufacturers included graphite coatings exterior to, for example, the cabling configured to communicate detector signals. However, the graphite gel used in the manufacturing process proved difficult to apply and remove. Because of these and other difficulties, manufacturers began substituting the graphite coatings with a coextruded conductive PVC sheath around, for example, their sensitive signal carrying cables.

SUMMARY OF THE DISCLOSURE

Embodiments of the present disclosure include the realization that coextruding the conductive PVC sheath around detector cables produces unnecessary rigidity in the resulting low noise cables. Accordingly, embodiments of the present disclosure seek to overcome the foregoing and other drawbacks through inclusion of one or more conductive polymer cords with sensitive signal carrying cables, such as, for example, the detector cables. The cords may be disposed around and adapted to drain triboelectric charge away from detector wires communicating low level detector signals from a noninvasive optical sensor. In one embodiment, the detector cables are twisted with the one or more polymer cords. In a particular embodiment, the polymer cords comprise hollow conductive polyvinyl chloride (PVC) tubes, although the cords may also comprise a flexible conductive vinyl or any suitable flexible conductive material recognizable to an artisan from the disclosure herein.

In other embodiments of the disclosure, some or all of an inner bundle of conductors configured to carry sensitive signals may be assembled marginally twisted or untwisted with one or more conductive cords, may be twisted, marginally twisted, or untwisted around one or more central conductive cords, combinations of the same or the like.

Accordingly, one embodiment of the disclosure includes an oximetry system capable of acquiring signals indicative of one or more physiological parameters of a patient. The system comprises a noninvasive sensor including a detector configured to detect light attenuated by body tissue and output a detector signal indicative of the detected light. The system also comprises a patient monitor configured to receive the detector signal and determine one or more physiological parameters the patient. The system also comprises a cable comprising an inner bundle including detector wires and at least one hollow conductive cord, the inner bundle being at least partially surrounded by an inner shield encased in an inner jacket, the inner jacket being at least partially surrounded by a plurality of outer wires, an outer shield and an outer jacket.

Another embodiment includes a cable for communicating sensitive low level signals. The cable comprises at least one wire including a conductor configured to communicate the sensitive signal and an insulator surrounding the conductor, and at least one hollow conductive cord assembled with said at least one wire. The cable also comprises a shield at least partially surrounding said assembly of at least one wire and at least one hollow conductive cord. The cable also comprises a jacket surrounding said shield, wherein said shield is capable of being set to a predetermined voltage to drain potential buildup of triboelectric charge on said jacket.

Yet another embodiment of the disclosure includes a method of manufacturing a cable comprising assembling an inner bundle including detector wires and at least one hollow conductive cord. The method also comprises at least partially surrounded the inner bundle with an inner shield, and surrounding said inner shield with an inner jacket.

For purposes of summarization, certain aspects, advantages and novel features are described herein. Of course, it is to be understood that not necessarily all such aspects, advantages or features need to be present in any particular embodiment.

BRIEF DESCRIPTION OF THE DRAWINGS

The following drawings and the associated descriptions are provided to illustrate embodiments of the present disclosure and do not limit the scope of the claims.

FIG. 2A is an exemplary cutaway side-view of the cable of FIG. 1, according to an embodiment of the disclosure.

FIG. 2B is an exemplary cross-sectional view of the cable of FIG. 1, according to an embodiment of the disclosure.

DETAILED DESCRIPTION

Embodiments of the present disclosure include a low noise oximetry cable configured to communicate low level sensitive signals between a sensor and a patient monitor. In an embodiment, one or more conductive cable cords are twisted with the sensitive signal carrying cables. The cords can advantageously comprise dummy wires, or very flexible hollow cables or tubes without an inner conductor. The conductive cords advantageously reduce interference or noise from corrupting the sensitive signals, by, for example, reducing or draining triboelectric charge buildup from around the sensitive signal carrying cables. Moreover, as the conductive cords do not carry and inner conductor, the conductive cords are individually very flexible, resulting in a twisted bundle that is more flexible and in some embodiments, may have a smaller outer diameter than the PVC sheath discussed above.

In an embodiment, the number cords twisted within the sensitive signal carrying cables is selected by balancing overall twisted bundle thickness, shape, size such as outer diameter, rigidity or flexibility, conductive or drain performance, cost, and the like. In an embodiment, the low noise cable includes from about one (1) to about eight (8) or more conductive cords twisted with one or more of the sensitive signal carrying cables or conductors. In another embodiment, the low noise cable includes from about two (2) to about seven (7) conductive cords twisted with one or more of the sensitive signal carrying cables or conductors. In yet another embodiment, the low noise cable includes two (2) conductive cords twisted with one or more of the sensitive signal carrying cables or conductors.

In other embodiments, the cords and/or the sensitive signal carrying cables may be assembled un-twisted or marginally twisted within the bundle, may entirely or partially surround sensitive signal carrying cables within the bundle, or the like. In still additional embodiments, one or more sensitive signal carrying conductors may be twisted, marginally twisted, or untwisted around one or more twisted, marginally twisted, or untwisted central cords.

To facilitate a complete understanding of the disclosure, the remainder of the detailed description references the drawings, wherein like reference numbers are referenced with like numerals throughout.

Figure 1:
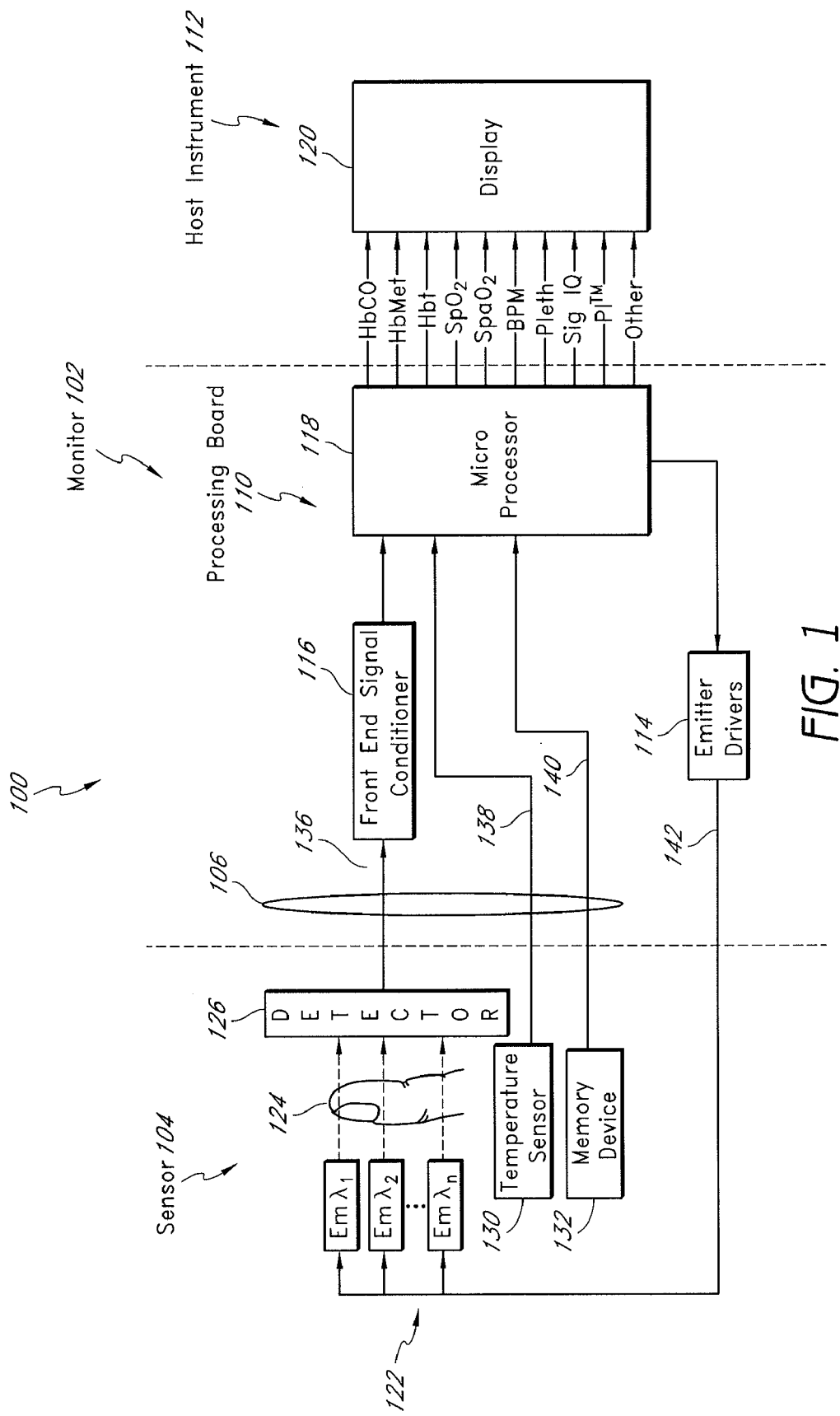
FIG. 1 is an exemplary block diagram of a patient monitoring system including a patient monitor and a noninvasive optical sensor communicating through a cable, according to an embodiment of the disclosure.

FIG. 1 illustrates an exemplary block diagram of a patient monitoring system 100 including a patient monitor 102 and a noninvasive optical sensor 104 communicating through a cable 106, according to an embodiment of the disclosure. The monitor 102 includes one or more processing boards 110 communicating with one or more host instruments 112. According to one embodiment, the board 110 comprises processing circuitry arranged on one or more printed circuit boards capable of installation into a handheld or other monitor, or capable of being distributed as an OEM component for a wide variety of host instruments monitoring a wide variety of patient information. As shown, the board 110 includes one or more emitter driving circuits 114, a front end 116, and a microprocessor 118.

The emitter driving circuit 114 outputs drive signals to the sensor 104. In an embodiment, the emitter driving circuit 114 may drive two (2) or more emitters capable of emitting light at two (2) or more wavelengths, or it may drive a matrix of eight (8) to sixteen (16) or more emitters capable of emitting light at eight (8) to sixteen (16) or more wavelengths.

The front end 116 conditions the signals, applies gain, converts signals to digital information, and the like, although an artisan will recognize from the disclosure herein that any or all of the functions of the drive circuit 114 and the front end 116 could be performed by other software or hardware components, or by the microprocessor 118. The microprocessor 118 may comprise one or more hardware or software components capable of executing instructions designed to control drive signals and to process incoming signal data related to the drive signals to determine desired physiological parameters of a monitored patient. In an embodiment, such parameters may include one or more of $SpO_2$, plethysmograph waveforms, perfusion quality index, pulse rate, HbCO, HbMet, HbT, $SpaO_2$, $HbO_2$, Hb, HbGu, water, the presence or absence of therapeutic drugs or abusive/recreational drugs, $CO_2$, $O_2$, pH levels, bilirubin, albumin, cyanmethemoglobin, and HbSulf, signal quality, signal confidence measures, trend data on one, some, all, or combinations of the foregoing, or the like. Moreover, the microprocessor 114 can determine when alarm conditions exist for alerting a caregiver to the current condition of the patient.

The host instrument 112 includes one or more display devices 120 capable of providing indicia representative of the calculated physiological parameters. In an embodiment, the host instrument 120 may advantageously comprise virtually any housing, including a handheld or otherwise portable monitor capable of conveying one or more of the foregoing measured or calculated parameters to a caregiver. The host instrument 120 may include audio or visual alarms that alert caregivers that one or more physiological parameters are falling below or above predetermined safe thresholds, or are trending in a predetermined direction (good or bad). The host instrument 120 may include indications of the confidence a caregiver should have in the conveyed data.

In an embodiment, the sensor 104 includes a plurality of emitters 122 irradiating the body tissue 124 with light, and one or more detectors 128 capable of detecting the light after attenuation by the tissue 124. The sensor 104 can also include a temperature sensor 130, such as, for example, a thermistor or the like, and a memory device 132. The memory 132 may comprise any one or more of a wide variety of memory devices known to an artisan from the disclosure herein, including an EPROM, an EEPROM, a flash memory, a ROM, a RAM, single wire memories, combinations, or the like. The memory device 132 can advantageously store some or all of a wide variety data and information, including, for example, information on the type or operation of the sensor, type of patient or body tissue, buyer or manufacturer information, sensor characteristics including the number of wavelengths capable of being emitted, number of emitters, emitter specifications, emitter operational characteristics, emitter drive requirements, history of the sensor temperature, current, or voltage, demodulation data, calculation mode data, calibration data, software such as scripts, executable code, or the like, sensor electronic elements, sensor life data indicating whether some or all sensor components have expired and should be replaced, encryption information, keys, indexes to keys, the parameters the sensor is intended to measure (e.g., HbCO, HbMet, etc.), monitor or algorithm upgrade instructions or data, some or all of parameter equations, combinations of the same, or the like.

As shown in FIG. 1, a plurality of conductors communicates signals to and from the sensor 104 and the board 110. These conductors include detector composite signal conductor(s) 136, temperature sensor conductor(s) 138, memory device conductor(s) 140, emitter drive signal conductor(s) 142, and the like. In an embodiment, some or all of these conductors are housed by the cable 106.

FIGS. 2A-2B illustrate an exemplary embodiment of a low noise patient cable 200, such as the cable 106 of FIG. 1, according to an embodiment of the disclosure. As shown, cable 200 includes an outer jacket 202, an outer shield 204, outer wires 206, an inner jacket 208, an inner shield 210, polymer cords 212, and detector wires 214, with the cords 212 and the detector wires 214 twisted. In an embodiment, the inner shield 210 is wrapped around the twisted bundle of cords 212 and detector wires 214, which is then encased by the inner jacket 208. The inner jacket 208 is then circumferentially surrounded by the outer wires 206, outer shield 204 and outer jacket 202, respectively.

As discussed in the foregoing, the number of cords 212 used in the twisted bundle can vary depending upon desired bundle thickness, shape, size such as outer diameter, rigidity or flexibility, conductive performance, cost, and the like. In an embodiment, to create a substantially circular shape to the inner bundle which is smaller than shapes created through the sheath, while maintaining or improving triboelectric drain and substantially improving flexibility, the inner bundle includes two (2) conductive cords 212 with two (2) detector wires 214, each detector wire comprising its inner conductor 218 and outer insulator 216. In an embodiment, the cords and wires are wound as if the cords were aligning substantially horizontally and the wires substantially vertically and then the resulting "+" shape was wound.

In an embodiment, the outer wires include conductors 222 and insulation 220. The shields 204 and 210 can also advantageously reduce EMI on each of and crosstalk between the outer wires 206 and the detector wires 214. It will be understood that when the shield 210 is grounded in use, or set to a predetermined threshold, that triboelectric charge buildup is drained off the jacket 208. The same triboelectric charge drain off the outer jacket 202 can occur when the shield 204 is grounded.

The outer conductor wires 206 are configured to carry multiple drive signals to the emitters 122. In an embodiment, the outer wires 206 communicate cathode and anode drive signals or the like. In an embodiment where the emitters 122 comprise a matrix emitter array, the outer wires 206 communicate row and column drive signals. In other embodiments, the outer wires also communicate temperature sensor signals, memory device signals, and the like. The detector wires 214 communicate a low level sensitive detector output signal(s) which is relied upon by the monitor 102 to determine patient physiological parameter data.

The components described in association with FIGS. 2A-2B can also share properties with the corresponding components described in association with FIGS. 3A-3B that follow below.

Figure 3B:
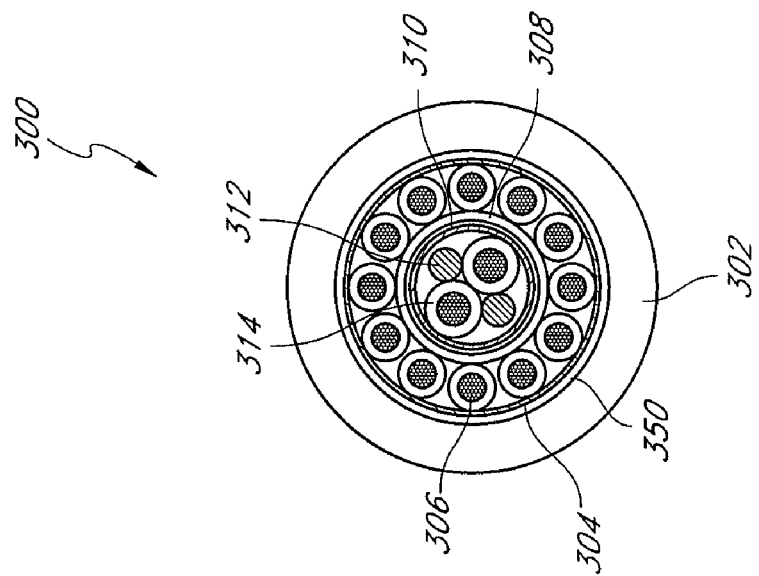
FIG. 3B is an exemplary cross-sectional view of the cable of FIG. 1 according to an embodiment of the disclosure.
Figure 3A:
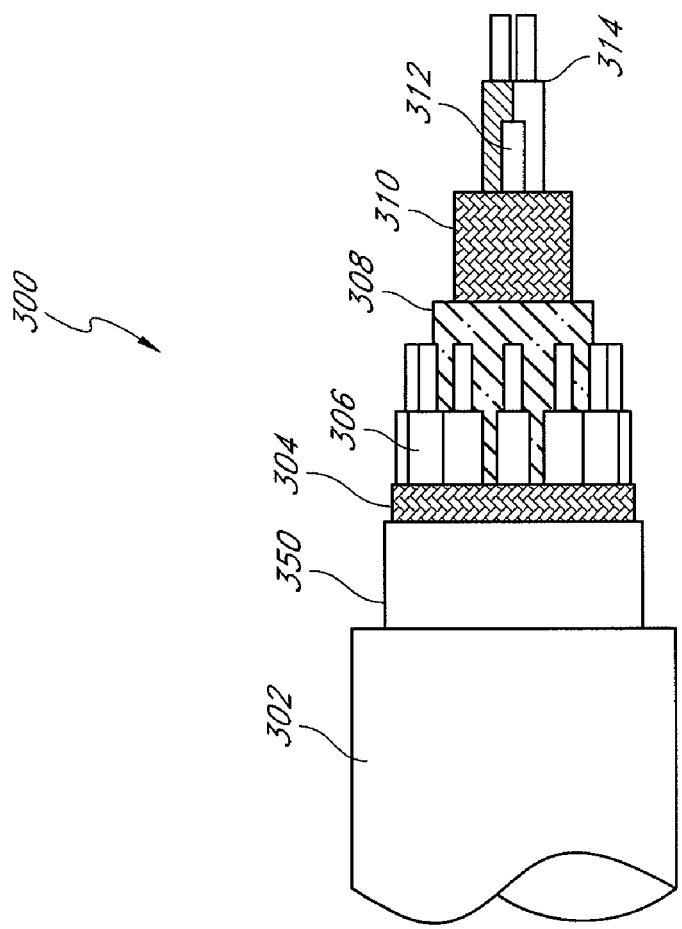
FIG. 3A is an exemplary cutaway side-view of the cable of FIG. 1, according to an embodiment of the disclosure.

FIGS. 3A-3B illustrate an exemplary embodiment of a low noise patient cable 300, such as the cable 106 of FIG. 1, according to an embodiment of the disclosure. As shown, the cable 300 of FIGS. 3A-3B includes an outer jacket 302, an outer separator 350, an outer shield 304, outer wires 306, an inner jacket 308, an inner shield 310, polymer cords 312, and detector wires 314, with the cords 312 and the detector wires 314 twisted or otherwise bundled together. In an embodiment, the inner shield 310 is wrapped around the twisted bundle of the cords 312 and the detector wires 314, which is then encased by the inner jacket 308. The inner jacket 308 is then circumferentially surrounded by the outer wires 306, the outer shield 304, the outer separator 350 and the outer jacket 302, respectively.

These components of the cable 300 shown in FIGS. 3A-3B can be designed, for example, by adjusting size, material, and relative placement, to meet performance or design objectives, such as, for example, outer diameter, flexibility, hardness, cost, degree of reduction of triboelectric noise, matching impedance, or other suitable objectives. Examples of these types of variations are disclosed in the following embodiments.

The design objectives can influence the outer diameter of the cable 300. Suitable dimensions for the outer diameter depend, for example, on the properties of the components within the cable. The cable 300 can vary in outer diameter, for example, in an embodiment, between 0.13 inches and 0.25 inches. In a more preferred embodiment, the outer diameter of cable 300 ranges from 0.135 inches to 0.21 inches. In an embodiment, the outer diameter of cable 300 is between 0.165 inches and 0.171 inches. The thickness of outer jacket 302 can also be adjusted, for example, by changing thickness and material to meet design objectives. In an embodiment, the outer jacket 302 has a thickness that ranges from 0.01 inches to 0.06 inches. In an embodiment, the outer jacket 302 has a nominal thickness of 0.022 inches. Outer jacket 302 can be constructed out of jacket materials such as, for example, Teflon®, other fluropolymers, Polytetrafluoroethelene (PFTE), Perfluoroalkoixy (PFA), Fluorinated ethylene propylene (FEP), Neoflon™, Kynar®, Polyvinylidene Fluride, Polyethylene, Polyvinylchloride (PVC), or other suitable jacket materials. In an embodiment, the outer jacket 302 is PVC. The material and thickness of outer jacket 302 can also be adjusted to meet hardness objectives. In an embodiment, the hardness of outer jacket 302 measures Shore 70A on a durometer using the ASTM D2240 type A scale.

The outer separator 350 can help provide flexibility to the cable and can also be adjusted to meet design objectives. The outer separator 350 can be made out of materials such as, for example, the jacket materials previously discussed or other suitable materials. The outer separator 350 can, for example, be made out of a material that will increase the flexibility of the cable by allowing the components housed inside the outer separator 350 to move somewhat independently of the outer jacket 302. In an embodiment, the outer separator 350 is Teflon®. In an embodiment, the outer separator 350 has a thickness that ranges from 0.001 inches to 0.01 inches. In a more preferred embodiment, the outer separator 350 has a thickness that ranges from 0.001 inches to 0.005 inches. In an embodiment, the outer separator 350 has a thickness of 0.002 inches. In an embodiment, the outer separator 350 is approximately 0.004 inches thick PTFE material.

The outer shield 304 can advantageously reduce EMI on each of and crosstalk between the outer wires 306. Outer shield 304 can be constructed of conductive materials or other suitable shield materials to meet performance or design objectives. An artisan will recognize from the present disclosure herein that copper, silver, or other suitable materials could be used as materials for the outer shield 304. In an embodiment, the outer shield 304 is constructed using braided copper strands. In an embodiment, the outer shield 304 is constructed using spiral strands. The thickness of the shield can also be adjusted to meet design objectives. In an embodiment, the outer shield 304 ranges in size from 44 AWG (American Wire Gauge) to 40 AWG. In an embodiment, the outer shield 304 is 44 AWG. In an embodiment, the outer shield 304 is 44 AWG, tinned copper, with a ninety percent minimum coverage.

The outer wires 306 can also be designed to meet certain performance or design objectives. In an embodiment, the outer wires 306 have an outer diameter that ranges from 0.005 inches to 0.03 inches. In a more preferred embodiment, the outer wires 306 have an outer diameter that ranges from 0.012 inches to 0.025 inches. In an embodiment, the outer wires 306 have an outer diameter of 0.022 inches. In an embodiment, the outer wires 306 are constructed out of wire that ranges in gauge from 32 AWG to 24 AWG. In a more preferred embodiment, the outer wires 306 are constructed out of wire that ranges in gauge from 32 AWG to 28 AWG. In an embodiment, the outer wires 306 are constructed out of 30 AWG wire. In an embodiment, the outer wires 306 have insulation that ranges in thickness from 0.002 inches to 0.01 inches. In an embodiment, the outer wires 306 have 0.005 inches of insulation. In an embodiment, the outer wires 306 are stranded 22/44 tinned copper. In an embodiment, the outer wires 306 are 25/44 tinned copper, insulated by 0.005 inch thick polypropylene, with an outer diameter of 0.022 inches. Although disclosed with reference to copper insulated by polypropylene, an artisan would recognize from the disclosure herein that other materials could also be used to construct the outer wires 306.

In addition to the outer wires 306 and inner jacket 308, the outer separator 350 can house filler materials to help meet design or performance objectives. The filler material can, for example, help create a round shape for the cable. The filler material can be materials such as, for example, Kevlar or other suitable materials. In an embodiment, the outer separator 305 houses Kevlar filler materials.

The inner jacket 308 can also be designed to meet certain design or performance objectives. The inner jacket 308 can be constructed, for example, out of the jacket materials previously disclosed or other suitable materials. In an embodiment, the inner jacket 308 is constructed from PFTE. The inner jacket can also be constructed by layering materials. In an embodiment, the inner jacket 308 is constructed with a single sintered PFTE wrap plus a single unsintered PFTE wrap. In an embodiment, the inner jacket 308 is PVC with a single PFTE wrap. The inner jacket 308 can also range in size, in an embodiment, from 0.001 inches to 0.01 inches. In a more preferred embodiment, the inner jacket 308 ranges in size from 0.002 inches to 0.008 inches. In an embodiment, the inner jacket 308 is a sintered PFTE film that is approximately 0.0012 inches thick and a single layer of unsintered PFTE film that is approximately 0.004 inches thick. In an embodiment, the overlap is minimized to minimize the overall diameter of the inner jacket 308 and the components it contains.

The inner shield 310 can advantageously reduce EMI on each of and crosstalk between the detector wires 314 and the outer wires 306. Inner shield 310 can be constructed of conductive materials or other suitable shield materials to meet performance or design objectives. An artisan will recognize from the present disclosure herein that copper, silver, or other suitable materials could be used as materials for the inner shield 310. In an embodiment, the inner shield 310 is constructed using braided copper strands. In an embodiment, the inner shield 310 is constructed using spiral copper strands. The thickness of the inner shield 310 can also be adjusted to meet design objectives. In an embodiment, the inner shield 310 ranges in size from 44 AWG to 40 AWG. In an embodiment, the inner shield 310 is 44 AWG, tinned copper, with a ninety percent minimum coverage.

The cords 312 can also be designed to meet performance or design objectives. The cords 312 can be constructed from semi-conductive PVC or other suitable materials. The material can be chosen or arranged, such as, for example, by twisting, to enhance low-noise characteristics. In an embodiment, the cords 512 are semi-conductive PVC and twisted. In an embodiment, the cords 312 have a size that ranges from 0.01 inches to 0.02 inches. In a more preferred embodiment, the cords have a size that ranges from 0.012 inches to 0.015 inches. The cords 312 In an embodiment, the cords 312 are approximately 0.015 inches plus or minus 0.003 inches.

The detector wires 314 can also be designed to meet performance or design objectives. The detector wires 314 can share properties with the outer wires 306. The thickness of the detector wires 314 can influence the performance or design objectives. In an embodiment, the gauge of the detector wires 314 ranges from 32 AWG to 24 AWG. In a more preferred embodiment, the gauge of the detector wires 314 ranges from 32 AWG to 28 AWG. In an embodiment, the detector wires are 30 AWG. In an embodiment, the detector wires are 28 AWG. In an embodiment, the outer wires 306 are constructed out of 30 AWG wire. In an embodiment, the detector wires 314 have insulation that ranges in thickness from 0.002 inches to 0.01 inches. In an embodiment, the detector wires 314 are have 0.007 inches of insulation. The detector wires 314 can be constructed out of materials such as, copper, silver, or other suitable materials. In an embodiment, the detector wires 314 are stranded 22/44 tinned copper. The insulation for detector wires 314 can be constructed out of materials such as polypropylene or other suitable materials. In an embodiment, the detector wires are 25/44 tinned copper, insulated by 0.007 inch thick polypropylene, with a nominal outer diameter of 0.027 inches.

The conductive cords have several advantages over a deposited graphite coatings and a coextruded PVC sheath for reducing triboelectric noise. For example, the cords may drain triboelectric induced charges away from the detector wire insulation 216 as well as or better than the graphite coating and PVC sheath. As with the PVC sheath, grouping of the cords with the detector wires 214 can increase the eventual signal quality output from signal processing circuitry, such as, for example, a differential amplifier. For example, use of the cords in a manner that maintains the close physical proximity of detector wires 214 tends to ensure external noise applied to the cable 200 is applied substantially equally (or common) to each conductor of the detector wires 214. Thus, a differential amplifier (not shown) of the monitor 102 can effectively filter the applied external noise through, for example, the amplifier's common mode rejection.

Thus, while exhibiting the same or superior advantageous characteristics of the coating or sheath, the cords are also easier to control, cause less rigidity (e.g., result in a more flexible bundle), and provide more straightforward processes during manufacturing that the coating or sheath. For example, the cords may be simply cut away at points of connectivity for the detector conductors 218 to circuit substrates or other electrical components. Moreover, inner bundles made with the hollow cords are often thinner than the foregoing coatings or sheath. For these and other reasons, the cords also advantageously provide less expensive manufacturing processes.

FIG. 2A also shows a braided inner bundle as an alternative to the twisted or wound inner bundle, the braided inner bundle having the cords 212 and the detector cables 214 braided together. However, an artisan will recognize from the disclosure herein that the inner bundle could advantageously be assembled in any manner of configuration to reduce costs, increase drain potential, create desired shapes, or the like. For example, the cords may be assembled braided, marginally braided, twisted, marginally twists, unbraided and untwisted, individually combined, twisted or braided, combinations of the same, or the like.

Although the low noise oximetry cable including conductive cords is disclosed with reference to its preferred embodiment, the disclosure is not intended to be limited thereby. Rather, a skilled artisan will recognize from the disclosure herein a wide number of alternatives for the cable. For example, the cords may not be hollow, may include a conductor or other conductive materials, may comprise only conductors of any suitably flexible material. Moreover, use of blank hollow cords may advantageously apply flexibility in a wide variety of applications, including cabling for virtually any medically monitored signals such as those invasively or noninvasively acquired signals relating to heart or brain activity or condition, spinal activity or condition, circulation parameters, tissue health, or the like. Moreover, an artisan will recognize from the disclosure herein that the cabling may comprises only one or more portions of the communication link between sensor components and monitor electronics. The cable may also be an integral part of a reusable, disposable or combination sensor. Moreover, the addition of conductive cords for shielding sensitive cabling may advantageously be applied generally to any and all cabling environments, and particularly in environments susceptible to triboelectric noise.

Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. An oximetry system capable of acquiring signals indicative of one or more physiological parameters of a patient, the system comprising:
    a noninvasive sensor including a detector configured to detect light attenuated by body tissue and output a detector signal indicative of the detected light;
    a patient monitor configured to receive the detector signal and determine one or more physiological parameters the patient; and
    a cable comprising an inner bundle including detector wires and at least one hollow conductive cord, the inner bundle being at least partially surrounded by an inner shield encased in an inner jacket, the inner jacket being at least partially surrounded by a plurality of outer wires, an outer shield and an outer jacket.

2. The system of claim 1, wherein the inner bundle comprises a twisted assembly of the at least one conductive cord and the detector wires.

3. The system of claim 1, wherein the inner bundle comprises a marginally twisted assembly of the at least one conductive cord and the detector wires.

4. The system of claim 1, wherein the inner bundle comprises a weaved assembly of the at least one conductive cord and the detector wires.

5. The system of claim 1, wherein the inner bundle comprises an untwisted twisted assembly of the at least one conductive cord and the detector wires.

6. The system of claim 1, wherein the inner bundle comprises the detector wires assembled around at least one central conductive cord.

7. The system of claim 1, wherein the inner bundle comprises two cords.

8. The system of claim 1, wherein the inner bundle comprises a twisted assembly of the at least one conductive cord and the detector wires.

9. An oximetry cable for communicating sensitive low level signals, the cable comprising:
    at least one wire including a conductor configured to communicate the sensitive signals and an insulator surrounding the conductor;
    at least one hollow conductive cord assembled with said at least one wire;
    a shield at least partially surrounding said assembly of at least one wire and at least one hollow conductive cord;
    a jacket surrounding said shield, wherein said shield is capable of being set to a predetermined voltage to drain potential buildup of triboelectric charge on said jacket;
    outer wires surrounding said jacket;
    an outer shield at least partially surrounding said outer wires; and
    an outer jacket surrounding said outer shield, wherein the at least one wire comprises one or more detector wires, the outer wires comprise emitter drive wires.

10. A cable for communicating sensitive low level signals, the cable comprising:
    at least one wire including a conductor configured to communicate the sensitive signals and an insulator surrounding the conductor;
    at least one hollow conductive cord assembled with said at least one wire;

a shield at least partially surrounding said assembly of at least one wire and at least one hollow conductive cord;

a jacket surrounding said shield, wherein said shield is capable of being set to a predetermined voltage to drain potential buildup of triboelectric charge on said jacket;

a first end configured to be coupled to a pulse oximetry sensor; and a second end configured to be coupled to a patient monitor, wherein the at least one wire comprises two detector wires, and wherein the outer wires comprise emitter drive wires, and wherein the cable comprises an oximetry cable.

11. The cable of claim 10, further comprising:

outer wires surrounding said jacket;

an outer shield at least partially surrounding said outer wires; and an outer jacket surrounding said outer shield.

* * * * *

UNITED STATES PATENT AND TRADEMARK OFFICE
CERTIFICATE OF CORRECTION

| | | |
|---|---|---|
| PATENT NO. | : 7,919,713 B2 | Page 1 of 1 |
| APPLICATION NO. | : 12/104350 | |
| DATED | : April 5, 2011 | |
| INVENTOR(S) | : Ammar Al-Ali et al. | |

It is certified that error appears in the above-identified patent and that said Letters Patent is hereby corrected as shown below:

At column 2, line 64, please delete "the patient." and insert therefore, --of the patient.--.

At column 6, line 62, please delete "fluropolymers," and insert therefore, --fluoropolymers,--.

At column 6, line 62, please delete "Polytetrafluoroethelene" and insert therefore, --Polytetrafluoroethylene--.

At column 6, line 63, please delete "(PFTE)," and insert therefore, --(PTFE),--.

At column 6, line 63, please delete "Perfluoroalkoixy" and insert therefore, --Perfluoroalkoxy--.

At column 6, line 64, please delete "Fluride," and insert therefore, --Fluoride--.

At column 8, line 2, please delete "PFTE." and insert therefore, --PTFE.--.

At column 8, line 5, please delete "sintered PFTE" and insert therefore, --sintered PTFE--.

At column 8, line 5, please delete "unsintered PFTE" and insert therefore, --unsintered PTFE--.

At column 8, line 7, please delete "PFTE" and insert therefore, --PTFE--.

At column 8, line 11, please delete "PFTE" and insert therefore, --PTFE--.

At column 8, line 12, please delete "PFTE" and insert therefore, --PTFE--.

At column 8, line 40, please delete "The cords 312".

At Claim 1, column 10, line 12, please delete "parameters the" and insert therefore, --parameters of the--.

Signed and Sealed this
Sixth Day of December, 2011

David J. Kappos
*Director of the United States Patent and Trademark Office*